United States Patent [19]
Bliss et al.

[11] Patent Number: 6,151,769
[45] Date of Patent: Nov. 28, 2000

[54] METHOD OF MAKING A SCINTILLATOR WAVEGUIDE

[75] Inventors: Mary Bliss; Richard A. Craig, both of West Richland; Paul L. Reeder, Richland, all of Wash.

[73] Assignee: Battelle Memorial Institute, Richland, Wash.

[21] Appl. No.: 08/924,357

[22] Filed: Sep. 5, 1997

Related U.S. Application Data

[63] Continuation-in-part of application No. 08/455,586, May 31, 1995, Pat. No. 5,704,890.

[51] Int. Cl.[7] .................................................. H01Q 13/00
[52] U.S. Cl. .................................. 29/600; 29/601; 29/825
[58] Field of Search ............................. 29/825, 600, 601; 600/1

*Primary Examiner*—Carl J. Arbes
*Attorney, Agent, or Firm*—Paul W. Zimmerman

[57] ABSTRACT

The present invention is an apparatus for detecting ionizing radiation, having: a waveguide having a first end and a second end, the waveguide formed of a scintillator material wherein the therapeutic ionizing radiation isotropically generates scintillation light signals within the waveguide. This apparatus provides a measure of radiation dose. The apparatus may be modified to permit making a measure of location of radiation dose. Specifically, the scintillation material is segmented into a plurality of segments; and a connecting cable for each of the plurality of segments is used for conducting scintillation signals to a scintillation detector.

3 Claims, 3 Drawing Sheets

METHOD OF MAKING A SCINTILLATOR WAVEGUIDE

This application is a continuation-in-part of application Ser. No. 08/455,586 filed May 31, 1995, now U.S. Pat. No. 5,704,890.

This invention was made with Government support under Contract DE-AC06-76RLO 1830 awarded by the U.S. Department of Energy. The Government has certain rights to the invention.

FIELD OF THE INVENTION

The present invention relates generally to a scintillator waveguide for sensing and/or measuring radiation delivery. More specifically the scintillator waveguide has an activator therein. The invention is especially useful for measuring therapeutic radiation delivered to a patient.

BACKGROUND OF THE INVENTION

Radiation is widely used for medical treatment. The primary radiation source is gamma or high energy x-rays. Thermal, epithermal, and high energy neutrons are also used.

It is critical that the amount and location of the radiation delivery be controlled as closely as possible. An error in intensity can either result in excessive tissue damage, or result in not accomplishing its intended purpose. An error in location can inadvertently cause damage to healthy tissue and organs, sometimes to critical organs such as eyes, brain, glands, etc, and cause severe debilitating damage and even death.

One method of estimating dose to a patient receiving thermal and epithermal neutron therapy is to insert a gold needle into the patient and then perform a partial exposure. The partial exposure is typically calculated to terminate at about the half-way point. The dose is generally terminated by the operator at the half-way point by turning off the source of radiation, or by closing off the radiation source. At that time the gold needle is removed and a radiation count is taken and dose calculations performed. The activation of the gold needle is assumed to be proportional to exposure to the gold needle. From the count rate taken on the gold needle the estimated dose received by the patient is calculated. Then the operator continues the radiation exposure to the full prescribed dosage. A disadvantage of this method is the invasiveness. In addition, gold needles may not be suitable for certain types of radiation.

Another method of estimating patient dose is with a stimulated phosphor. Disadvantages of using a stimulated phosphor include use of an infrared laser or other infrared light source to heat the phosphor. Since an infrared source is required, real-time measurement is not practical.

Another approach to estimating dose is the use of a phantom prior to irradiation. A phantom is in essence a model made of "equivalent material" to the object to be examined. A limitation of this method is that it is indirect and is subject to variation in the patient(s) compared to the phantom.

Accordingly, there is a need for an apparatus for measuring a non-invasive, real-time actual patient radiation dose.

SUMMARY OF THE INVENTION

The present invention is an apparatus for detecting a ionizing radiation, having:
a waveguide having a first end and a second end, the waveguide formed of a scintillator material wherein the therapeutic ionizing radiation isotropically generates scintillation light signals within the waveguide. This apparatus provides a measure of radiation dose.

The apparatus may be modified to permit making a measure of location of radiation dose. Specifically, the scintillation material is segmented into a plurality of segments; and a connecting cable for each of the plurality of segments is used for conducting scintillation signals to a scintillation detector.

DESCRIPTION OF THE PREFERRED EMBODIMENT(S)

Figure 1:
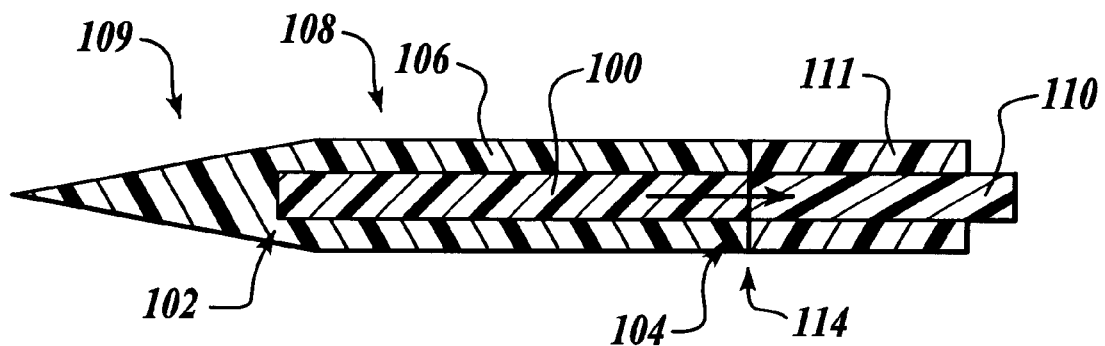
FIG. 1: Is a cross section of a probe according to the present invention.

Referring to FIG. 1, the apparatus of the present invention for detecting ionizing radiation has a first waveguide 100 having a first end 102 and a second end 104, the first waveguide 100 formed of a scintillation material wherein the therapeutic ionizing radiation isotropically generates scintillation light signals within the waveguide 100. The scintillation material may be organic, for example plastic including but not limited to polyvinyltoluene, polystyrene, or mixtures. The plastic may be made with or without wavelength shifters, or inorganic, for example lithium silicate glass, and halide scintillators, for example CsI and/or $BaF_2$.

In a preferred embodiment, the scintillation material is doped with an activator selected from the group consisting of $_3Li^6$, $Ce^{+++}$ and combinations thereof. Epithermal neutrons are preferably detected with glass doped with $_3Li^6$, or with lithium silicate glass doped with light emitting $Ce^{+++}$ ion.

Cerium-activated $_3Li^6$-loaded glasses are fabricated by melting the raw materials under a reducing atmosphere control to prevent the formation of $Ce^{4+}$. Any reducing atmosphere may be used including but not limited to carbon monoxide mixed with carbon dioxide, preferably a non-explosive mixture of CO and $CO_2$, wet hydrogen (i.e. hydrogen gas with water vapor), preferably saturated hydrogen, argon with 4 vol % hydrogen, and mixtures. The glass melt is quickly cooled by pouring onto a chilled metal plate. This glass can be made into a scintillating fiber form by remelting shards and drawing the fiber from the melt, coating the fresh fiber with an appropriate organic resin and polymerizing the resin on the fiber. Successful fabrication of neutron-sensitive scintillating glass is critically dependent upon control of the oxidation state during the glass melt and fiberizing processes.

When using the present invention to detect the therapeutic dose of gammas and x-rays, the preferred scintillation material depends upon the intensity of radiation to be measured. For large intensity radiation (above about a few rem/minute), the lowest possible Z number should be used to minimize the production of Compton electrons which can cause damage to the patient. A high Z material increases the production of Compton electrons with increasing radiation level. For small intensity radiation (below about a few millirem/hr), the use of high Z number scintillator material improves the detection efficiency. Thus, for maximum detection efficiency, it is preferred to select the highest possible Z material that may be tolerated under a medical protocol. For medium intensity radiation, the choice of scintillator material may be governed by other considerations, for example light output of the scintillator materials and other optical parameters.

Because neutron events produce approximately an order of magnitude more photoelectrons than gamma-ray interactions, a threshold may be chosen to separate neutron events from gamma and other radiation events.

In a preferred embodiment, the first waveguide 100 has a coating 106 encasing the first waveguide 100, thereby forming a probe 108. The coating 106 is preferably a polymer to provide a low activation potential in a radiation field. Polymers specifically preferred are from the group of polysilicones, polypropylenes, polyethylenes and combinations thereof. The first end 109 may be of any shape, but may be tapered as shown for use of the probe 108 as an insertion probe.

The waveguide 100 scintillation material produces light signals that may be transmitted over long distances. Accordingly, light signals must propagate through the scintillation material and any optical cable 110. To achieve long distance transmission of light signals, the light must be fully contained within the scintillation material and the optical cable 100. This containment is achieved in practice via total internal reflection.

Figure 2:
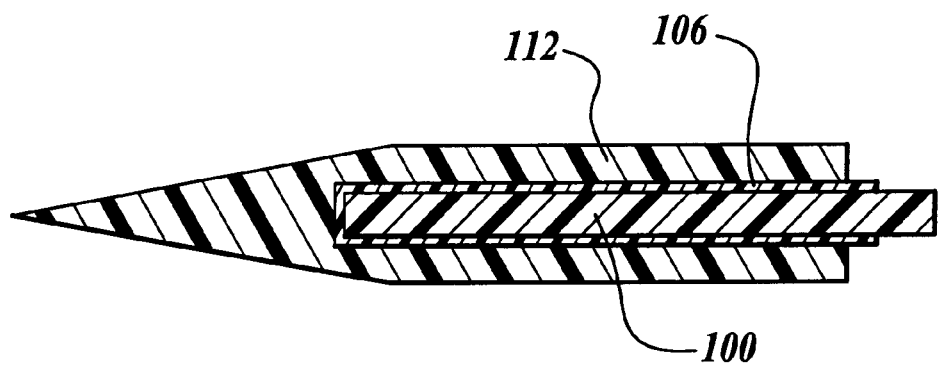
FIG. 2: Is a cross section of a waveguide having a cladding and a protective sheath.
Figure 3:
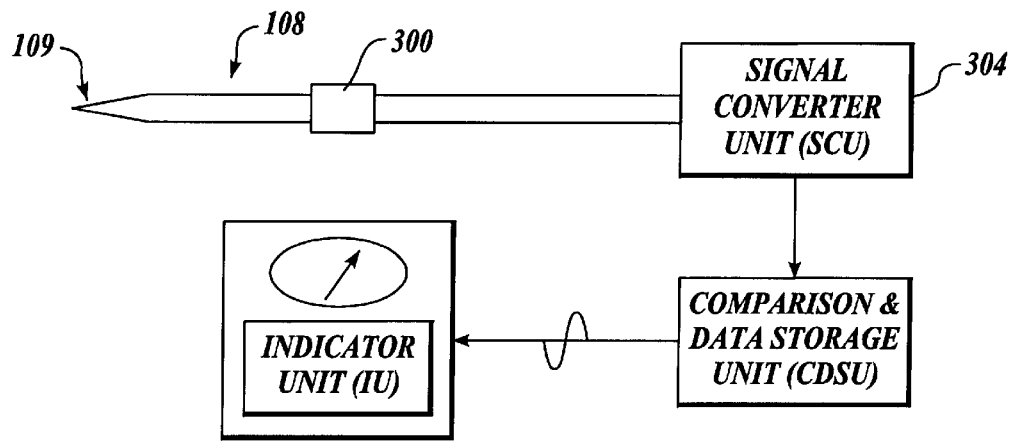
FIG. 3: Is a block diagram illustrating the components of the probe assembly and components used for signal analysis.

Total internal reflection of the light signals of a given wavelength range occurs when two conditions are met: 1) the refractive index of the material surrounding the scintillation material and/or optical cable 100 is smaller than the refractive index of the scintillation material and/or optical cable 100 itself, and 2) the angle of the light signal is smaller than some angle which is determined by the two refractive indices. When these two conditions are met in a waveguiding geometry, i.e., the refractive index of the core is greater than that of the cladding, the radiation will propagate with loss only determined by the absorptive properties of the two materials. In selective circumstances, the cladding may be air, but in most cases, it is necessary and preferred to surround the waveguide 100 scintillation material and the optical cable 110 with a coating or cladding 106, 111 with an appropriate refractive index. In some cases, it may be desirable to provide a cladding 106 that is further surrounded by a protective sheath 112 as shown in FIG. 2.

The first waveguide 100 may be attached to a first optical cable 110 attached to the second end 104 with an optical interface 114 at the contact between the second end 104 and the first optical cable 110.

At the optical interface 114 the light signals will either enter the first optical cable 110 or be reflected at the optical interface 114. The reflection is minimized when the difference between the refractive indices of the scintillator material and the first optical cable 110 is minimized and when the quality of the interface is maximized. The light signal entering the first optical cable 110 will be transmitted without reflective loss only if the ray angles in the second fiber meet the condition for total internal reflection. Therefore, it is important to the successful practice of the invention that the refractive indices of the scintillating material of the waveguide 100 and the first optical cable 110 be properly matched.

The opposite end of the first optical cable 110 is preferably connected to a first port on a scintillation detector (not shown) for receiving optical scintillation from the first waveguide 100. The first optical cable 110 preferably has a protective outer sheath or coating 111.

The scintillation detector may be any scintillation detector which converts the optical signal to an electrical signal including but not limited to photomultiplier tube, and avalance photodiode. When using a photomultiplier tube for measuring neutrons, the photomultiplier tube is preferably operated at a negative high voltage of about 1000 V. The photoelectron signal is pick off the last dynode with a high-speed electronics circuit. The high-speed electronics circuit has a preamplifier connected to a 60-ns integrator which is followed by a discriminating and pulse-counting circuit. The discriminating circuit has a threshold set at least about 1.25 photoelectrons to minimize photomultiplier tube dark count and gamma-ray sensitivity. In a reactor environment, the threshold needs to be set higher for the intense gamma-ray fields therein.

Figure 4:
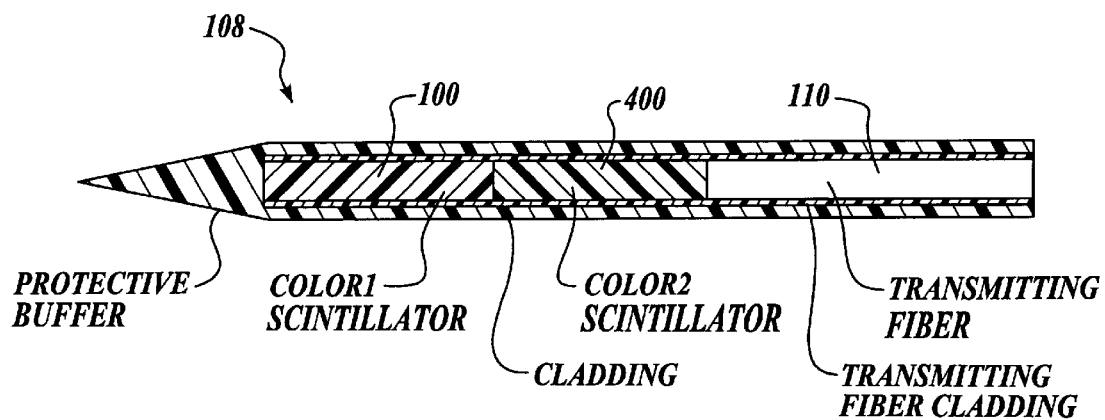
FIG. 4: Is a cross-section of a probe having two waveguides.

The apparatus of the present invention may be used for determining the relative location with respect to the patient of the therapeutic radiation as well as a dose level. In FIG. 4, in addition to the first waveguide 100, a second waveguide 400 is added. In order to distinguish between scintillation from the first waveguide 100 and the second waveguide 400, the second waveguide 400 is constructed to scintillate a different color light compared to the first waveguide 100. Different color light scintillation is achieved by using different activators, for example a rare earth, (e.g. cerium ($Ce^{+++}$), erbium) in glasses or crystals; sodium or thallium in alkali halide crystals such as cesium iodide; or different wavelength shifters, for example, 3-hydroxy-flavone. The scintillation detector 300 or 304 must then be able to distinguish between light signals of the different colors.

EXAMPLE 1

Figure 5A:
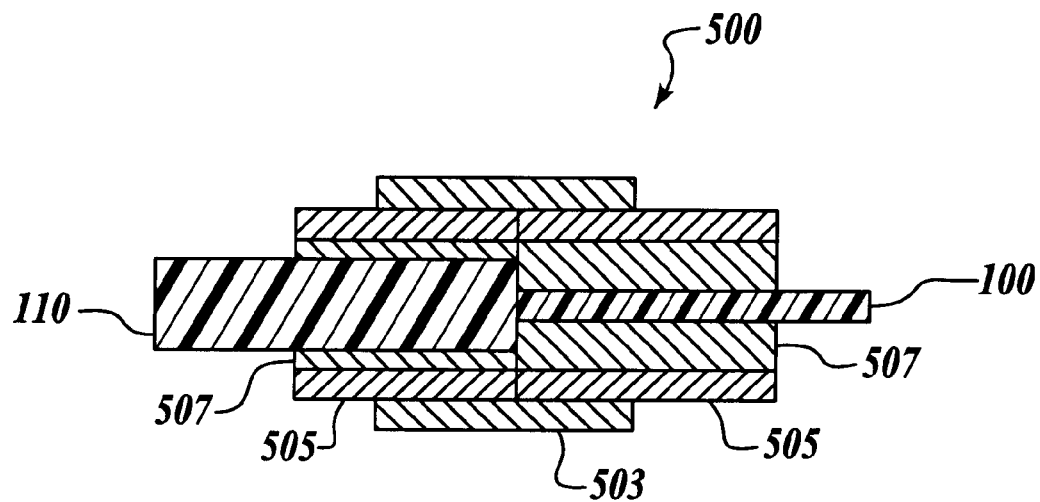
FIG. 5a: is a cross-section of a probe using a commercial fiber optic connector.
Figure 5B:
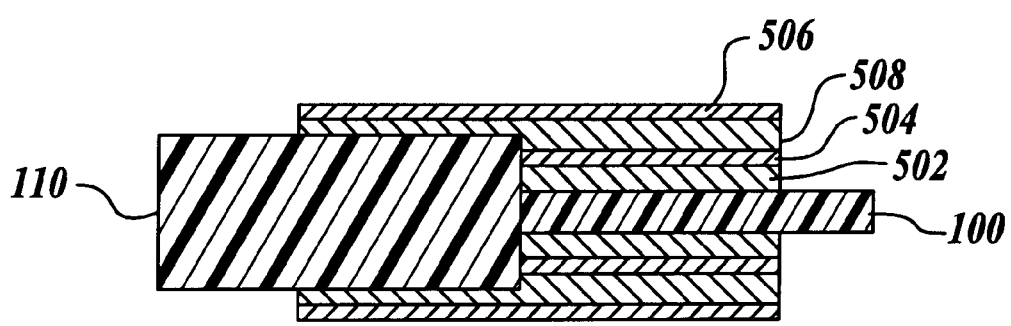
FIG. 5b: is a cross-section of a probe with a clad waveguide.

An experiment was conducted to demonstrate radiation detection of the present invention. Two probes were constructed as shown in FIG. 5a, 5b. In FIG. 5a, the first waveguide 100 was mounted in a commercial fiber-optic connector 500. The commercial fiber-optic connector 500 has an outer housing 503 that holds two inner sleeves 505 into which are inserted the first waveguide 100 and the first optical cable 110. Epoxy 507 was used to secure the first waveguide 100 and the first optical cable 110 in the inner sleeves 505. In FIG. 5b, the first waveguide 100 with its cladding 502 is glued with silicon into a first glass capillary 504 as a waveguide assembly. The waveguide assembly is glued within a second capillary 506 together with an adjoining commercial clad optical fiber 110. The second capillary 506 extends over the commercial optical fiber 110 and any annular space therebetween is filled with silicon 508.

Fluxes typical of boron neutron capture therapy (about $10^{19}$ $n/cm^2/sec$) and an epicadmium flux have been measured with both probes for periods in excess of an hour. The response of the waveguide 100 was linear with reactor power at the higher ($\geq 10$ kW) reactor powers. At lower powers (<10 kW), the residual gamma-ray flux was large enough that the detector response was not linear with reactor power. Even though the pulse-height threshold was not optimized for gamma-ray rejection, the gamma-ray interference was still quite small. The gamma-ray sensitivity would be reduced by more than an order of magnitude by increasing the threshold bias by 50%.

No degradation was observed after leaving a waveguide 100 in the reactor gamma-ray field for 16 hours.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method for making a waveguide for radiation detection, comprising the steps of:

(a) melting a scintillator material and an activator selected from the group consisting of $_3Li^6$, $Ce^{+++}$ and combinations thereof in a reducing atmosphere in a doped scintillator melt;

(b) forming the doped scintillator melt into a waveguide by pouring the doped scintillator melt onto a chilled metal plate and forming shards then remelting the shards and drawing the waveguide from the melted shards.

2. The method as recited in claim 1, further comprising the step of coating the waveguide with an organic resin and polymerizing the organic resin.

3. The method as recited in claim 1, wherein said reducing atmosphere is selected from the group consisting of carbon monoxide mixed with carbon dioxide, wet hydrogen, argon with 4 vol % hydrogen, and mixtures.

* * * * *